United States Patent [19]

Takenaka et al.

[11] Patent Number: 4,898,573
[45] Date of Patent: Feb. 6, 1990

[54] BLOOD COMPONENTS COLLECTOR UNIT

[75] Inventors: Yoshinori Takenaka, Oita; Hirokazu Fukumi, Fuchu; Sadayoshi Sekiguchi, Sapporo, all of Japan

[73] Assignee: Asahi Medical Co., Ltd., Tokyo, Japan

[21] Appl. No.: 114,020

[22] Filed: Oct. 29, 1987

[30] Foreign Application Priority Data

Oct. 29, 1986 [JP] Japan .................. 61-255922
Sep. 1, 1987 [JP] Japan .................. 62-216517

[51] Int. Cl.$^4$ .............................. A61M 1/34
[52] U.S. Cl. ........................ 604/6; 604/410
[58] Field of Search ....................... 604/4–6, 604/262, 408–410, 148, 200, 244, 905; 210/257.2

[56] References Cited

U.S. PATENT DOCUMENTS

| | | | |
|---|---|---|---|
| 2,702,034 | 2/1955 | Walter. | |
| 3,064,647 | 11/1962 | Earl | 604/410 |
| 4,294,247 | 10/1981 | Carter et al. | 604/905 |
| 4,330,410 | 5/1982 | Takenaka et al. | 210/767 |
| 4,340,049 | 7/1982 | Munsch | 604/244 |
| 4,397,747 | 8/1983 | Ikeda | 310/651 |
| 4,410,321 | 10/1983 | Pearson et al. | 604/410 |
| 4,578,056 | 3/1986 | King et al. | 604/6 |
| 4,605,503 | 8/1986 | Bilstad et al. | 210/651 |
| 4,639,243 | 1/1987 | Schmidt et al. | 604/6 |
| 4,668,399 | 5/1987 | Duggins | 210/651 |
| 4,680,025 | 7/1987 | Krugger et al. | 604/6 |

FOREIGN PATENT DOCUMENTS

| | | |
|---|---|---|
| 114698 | 8/1984 | European Pat. Off. . |
| 56049157 | 4/1979 | Japan . |
| 8400015 | 1/1984 | PCT Int'l Appl. .............. 210/433.2 |
| 2035133 | 6/1980 | United Kingdom . |

Primary Examiner—Dalton L. Truluck
Assistant Examiner—Denise W. DeFranco
Attorney, Agent, or Firm—Birch, Stewart, Kolasch & Birch

[57] ABSTRACT

There is disclosed a blood components collector unit comprising a cannula, a blood collection bag and a membrane type blood components separator which are connected in this order through tubes, and also comprising a plasma collection reservoir and a blood cell collection reservoir, both of which are connected to the blood components separator through tubes, wherein each connection through each tube is in a fixed fashion, thereby providing a unified connection, and wherein the blood collector unit is packed in a container in a sterile state. By the use of the unit of the present invention, whole blood can be collected and separated into blood components easily at a shortened period of time without any cumbersome preparatory operations. In addition, since the unit of the present invention is compact and light in weight and can be used without any other auxiliary apparatus, the unit can be conveyed to and used in any places, such as in automobiles and outdoors. Further, the time of restraining a whole blood donor can be decreased, leading a less burdening of the donor with a great advantage.

10 Claims, 3 Drawing Sheets

BLOOD COMPONENTS COLLECTOR UNIT

BACKGROUND OF THE INVENTION

1. Field of the Invention

The present invention relates to a blood components collector unit which is useful for separately collecting blood components, particularly for separately collecting plasma and blood cell-enriched blood from the blood of a healthy human.

2. Discussion of the Prior Art

In recent years, there has been an increase in demand for transfusions of blood components. Conventionally, several methods have been proposed for separately obtaining blood components. One of the methods, which was first proposed, was the so-called centrifugal separation method in which whole blood is taken from a donor and then the blood is subjected to centrifugation, causing the blood to separate into plasma and blood cell components.

On the other hand, there is a demand for only the plasma component of blood. For meeting the demand, there have been proposed methods for collecting only plasma from whole blood, for example, (a) the so-called extracorporeal circulation method in which a membrane type plasma separator is directly connected to a vein of a donor through pumping means, and whole blood is withdrawn from the donor with aid of the pumping means and conveyed to the membrane type plasma separator in which the blood is separated into plasma and blood cell-enriched blood, and the separated plasma is then collected while the blood cell-enriched blood is returned into the donor, and (b) the so-called dropping method in which whole blood is withdrawn out of the donor utilizing the force of gravity and conveyed to a membrane type plasma separator in which the blood is separated into plasma and blood cell-enriched blood, and the separated plasma is then collected while the blood cell-enriched blood is returned into the donor utilizing the force of gravity in the same manner as in installation.

However, the above-mentioned centrifugal separation method has a disadvantage in that a centrifugal separator which is an elaborate apparatus needs to be used. Further, in this method, since the respective blood components are unstably separated into two layers due to the difference in specific gravity and separately collected by manual operation, the method is not only disadvantageous from viewpoints of ease in operation, cost and simplicity, but also has a high possibility that the collected plasma disadvantageously contains platelets and leukocytes, leading to an instability in quality of the collected plasma.

Further, in practicing either the extracorporeal circulation method or the dropping method, the donor and the plasma separator are kept connected directly to each other during the plasma separating operation and, hence, the rate of blood flow through the plasma separator must be set so as not to burden the body of the donor. Therefore, it is difficult to set the supply rate of the blood to the capacity of the plasma separator, so that the capacity of the plasma separator cannot be fully exercised. Moreover, any of the above-mentioned methods is practiced so as to collect plasma in an amount as much as 400 to 600 ml and, therefore, it takes a considerably long time for completion of the plasma collecting operation. Hence, the donor must be restrained for a long time until completion of the operation.

Further, in any of the above-mentioned methods, during the operation it is necessary to introduce an anticoagulant to the blood at a predetermined flow rate and, hence, even the dropping method, which is advantageous in that the method can be practiced using a simple apparatus, disadvantageously needs to involve the additional use of equipment for introducing an anticoagulant to the blood taken from the donor. Moreover, in practicing any of the above-mentioned methods, the donor and the plasma separator need to be connected to each other throughout the plasma separation operation and, therefore, it is disadvantageously necessary to involve the additional use of means for safety such as a bubble detector and the like. Furthermore, in any of both methods, the blood cell-enriched blood is returned to the donor and, hence, there is a disadvantage in that the anticoagulant unavoidably enters the body of the donor together with the returned blood.

The so-called dropping method and an apparatus for collecting plasma to be used for the method are disclosed for the first time in European Patent Application Publication No. 0114698. In this publication, it is described that the conventional extracorporeal circulation method employing a membrane type plasma separator has disadvantages in that it is necessary to use various equipments such as a pump and a safety monitor, and that it is much more costly than that of the centrifugal method. The object of the invention of the above European Patent Application is to realize collection of plasma from the donor, while enjoying a high separation performance of a membrane type plasma separator, at a cost as low as possible and using an apparatus as simple as possible. The dropping method described in the above European Patent Application Publication No. 0114698 is far simpler in operation than the other conventional techniques for collecting blood components separately and the apparatus used in the dropping method also is simple as compared with those used in the other conventional techniques.

The dropping method is excellent in its principle. However, as described hereinbefore, the plasma separation system disclosed in the European Patent Application Publication No. 01146980 has the following various disadvantages: (1) additional means are needed for introducing an anticoagulant to the blood taken from the donor, (2) since the rate of withdrawal of whole blood from the donor is preferentially set, the rate of plasma separation is necessarily limited according to the flow rate of whole blood, and (3) there is disclosed no measures for recovering valuable human blood which, after completion of the operation of separating blood components, inevitably remains in the circuit of the apparatus, particularly in the membrane filter plasma separator.

Moreover, the apparatus of the above European Patent Application Publication No. 0114698 has a major disadvantage in that it requires cumbersome various preparatory operations before the blood components collecting operation. That is, (1) various components of the apparatus such as the filtration unit and reservoirs need to be provided separately and must be rinsed before use with an electrolyte solution containing an anticoagulant, (2) the anticoagulant contained in the plasma collection bag and the blood cell collection bag needs to be thrown out before use, and (3) the components of the apparatus need to be assembled just before use. Moreover, during the operation, the apparatus is not closed at the inlet for introducing an anticoagulant from outside and, hence, it is possible that the separated blood plasma and blood cell components are contaminated with various germs.

SUMMARY OF THE INVENTION

The present inventors have made extensive and intensive studies with a view to developing a blood components collector unit which is free from the above-mentioned drawbacks. As a result, it has been found that by providing a blood collection bag containing an anticoagulant between a cannula and a blood components separator to collect and temporarily pool whole blood from a donor in the bag before separating the blood into blood components, the donor is no longer required to be restrained for such a long time as in the case of the above-mentioned conventional dropping method, and there is no need to provide an additional equipment for introducing an anticoagulant. Further, it has been found that since there is no longer needed any additional means for introducing an anticoagulant, the blood components separation system becomes excellent in closure characteristics as compared with the apparatus used in the above-mentioned conventional dropping method. Furthermore, it has been found that by connecting a cannula, a blood collection bag containing anticoagulant, a blood components separator and reservoirs for collecting blood components through tubes in a fixed fashion to render the entire apparatus in a unified form, it advantageously becomes unnecessary to conduct cumbersome preparatory operations such as rinsing and assembling just before use. Based on the above-mentioned findings, the present invention has been completed.

Accordingly, an object of the present invention is to provide a novel blood components collector unit which is extremely useful for separately collecting plasma and blood cell-enriched blood from whole blood by an extremely simple operation with high efficiency.

Another object of the present invention is to provide a novel blood components collector unit of the type mentioned above, which is also effective for not only reducing the time of restraining the donor but also making no waste of valuable human blood.

The foregoing and other objects, features and advantages of the present invention will be apparent from the following detailed description taken in connection with the accompanying drawings.

DETAILED DESCRIPTION OF THE INVENTION

According to the present invention, there is provided a blood components collector unit comprising:
a cannula,
a blood collection bag connected to said cannula through a first tube, said blood collection bag containing an anticoagulant,
a membrane type blood components separator having a plasma outlet and a blood cell outlet, which separator is connected to said blood collection bag through a second tube,
valve means positioned intermediate the length of and within said second tube, which is in the closed state and has opening means for opening said valve means,
said opening means being adapted to permit the opening of the valve means by manual manipulation from outside of said second tube,
a plasma collection reservoir for collecting plasma, and
a blood cell collection reservoir for collecting blood cell-enriched blood,
said plasma collection reservoir and said blood cell collection reservoir being connected to said blood components separator at said plasma outlet through a third tube and at said blood cell outlet through a fourth tube, respectively,
wherein each connection through each tube at both ends thereof is in a unified fashion, thereby providing unified connection,
and wherein said collector unit is packed in a container in a sterile state.

Figure 1:
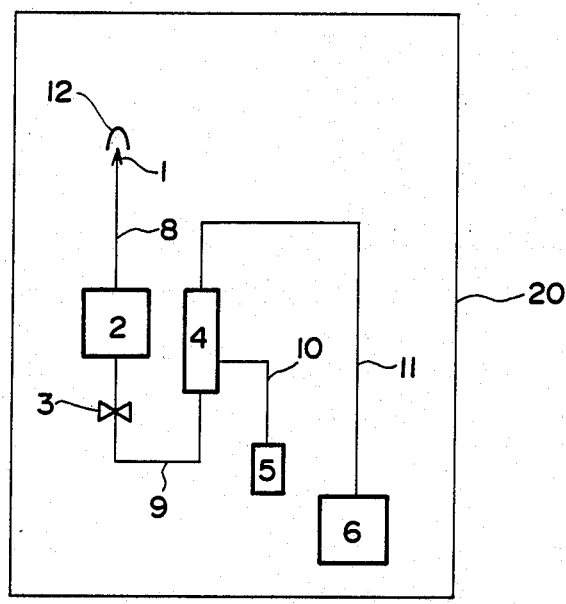
FIG. 1 is a schematic diagram of a blood components collector unit embodying the present invention, which is packed in a container in a sterile state.

Referring now to FIG. 1 in which there is shown a schematic diagram of a blood components collector unit embodying the present invention which is packed in a container in a sterile state, cannula 1 is connected with a blood collection bag 2 by a first tube 8. As the cannula 1, there is generally employed a hollow needle which is customarily used for collecting blood from a vein.

The blood collection bag 2 contains an anticoagulant in order to prevent coagulation of whole blood which is collected in the blood collection bag 2 from a vein of a donor through the cannula 1 and tube 8.

Examples of suitable anticoagulants include compositions such as an "ACD" solution and a "CPD" solution. The ACD solution comprises glucose, trisodium citrate and citric acid. The composition of the ACD solution varies according to country. In Japan, there is employed an ACD solution containing 22.0 g trisodium citrate, 8.0 g citric acid and 22.0 g of glucose per 1000 ml. The CPD solution contains 26.30 g of trisodium citrate, 3.27 g of citric acid, 23.20 g of glucose and 2.51 g of sodium dihydrogen phosphate per 1000 ml.

The amount of anticoagulant contained in the blood collection bag 2 may be enough for preventing the quantity of whole blood, which is intended to be collected, from coagulation. The amount of the anticoagulant varies not only according of the quantity of whole blood which is intended to be collected but also the type and composition of the anticoagulant. For example, in the case of an ACD solution adopted in Japan, the amount of the anticoagulant may generally be 15 ml per 100 ml of whole blood. In the case of a CPD solution adopted in Japan, the amount of the anticoagulant may be 14 ml per 100 ml. Where the membrane filter in the blood components separator 4 has previously been in a state moistened with an anticoagulant as will be explained later, the amount of an anticoagulant to be charged in the blood collection bag 2 may be less than the amount of an anticoagulant to be used for preserving the entire quantity of the whole blood to be collected by the amount of an anticoagulant used for moistening the membrane filter.

The blood collection bag 2 may also contain a predetermined amount of a sterile gas. Examples of the sterile gas include sterile air, sterile nitrogen gas and the like. The amount of the sterile gas to be contained may preferably be substantially equal to the total volume of portions in the present blood component collector unit, in which portions blood may remain even after completion of the separation operation. These portions mainly include the blood components separator 4. The amount of a sterile gas to be used may be determined mainly according to the volume of hollow portions of the membrane filter of the blood components separator 4. For example, where the membrane filter of a blood components separator 4 has a surface area of about 0.1 to about 0.2m$^2$, the suitable amount of the sterile gas is about 25 to 35 ml. In operation, as will be described later, after completion of the separation operation, the blood collection bag 2 is compressed in order for the sterile gas to push the whole blood and blood components, which remain in various portions of the present unit, if any, so that all the whole blood taken from the donor can be completely separated and collected.

Figure 3:
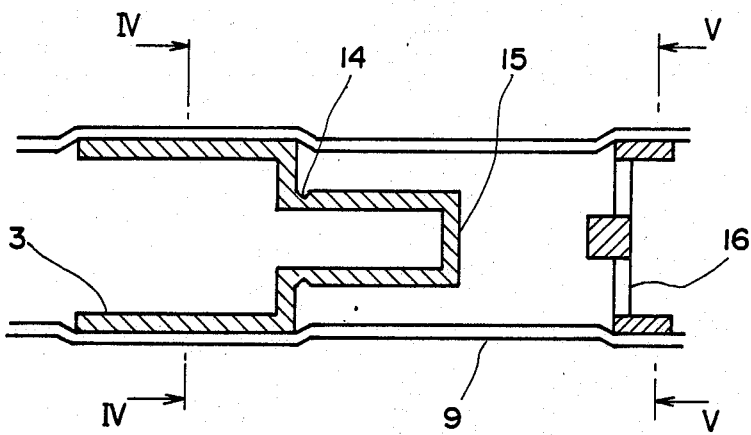
FIG. 3 is a longitudinal sectional view of one form of valve means which is positioned within a portion of a second tube designated by numeral 9 in FIG. 1, shown with the second tube partly cut-away.
Figure 4:
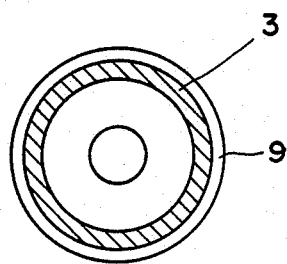
FIG. 4 is a cross-sectional view taken along the line IV—IV of FIG. 3.
Figure 5:
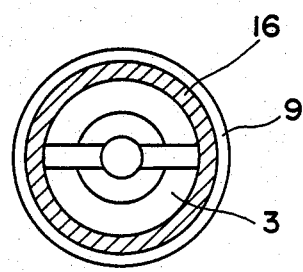
FIG. 5 is a cross-sectional view taken along the line V—V of FIG. 3.

A membrane type blood components separator 4 is connected to the blood collection bag 2 through a second tube 9. In FIG. 1, the blood components separator 4 is connected to the blood collection bag 2 on its side remote from the cannula 1. However, a portion of the blood collection bag 2 to which the blood components separator 4 is to be connected through a second tube 9 is not critical and the separator 4 may be connected to the blood collection bag 2 at any portion thereof other than the portion to which the cannula 1 is connected, as long as the separator 4 is so designed as to conform to the intended connection. Intermediate the length of and within the second tube 9, valve means, for example as shown in FIGS. 3 and 4 but not be limited thereto, is positioned in the closed state so that a predetermined quantity of whole blood may be collected and temporarily pooled in the bag 2 before whole blood flows into the blood components separator 4. In FIG. 3, there is shown a longitudinal sectional view of one form of valve means employed in the present invention. FIG. 4 shows a cross-sectional view taken along the line IV—IV of FIG. 3. Valve means 3 has opening means 15 for opening the valve means. The opening means 15 is adapted to permit the opening of the valve means by manual manipulation from outside of the second tube 9. For this purpose, the valve means 3 comprises a cylindrical body whose one end is opened and a small-diametered cylindrical closure member 15 (opening means) integrally formed with the cylindrical body and connected to an opening of the other end of the cylindrical body through a recessed angular portion 14. For opening the valve means 3, the closure member 15 is snapped at the recessed portion 14 by manual manipulation from outside of the second tube 9. The cylindrical body 3 and the closure member 15 integrally formed therewith are usually made of a suitable synthetic resin material. The material of the valve means is not critical and any materials may be used as long as it is rigid and heat resistant and can be snapped. Generally, polyvinyl chloride, polycarbonate resin, polypropylene or the like may be used. FIG. 5 shows a cross-sectional view taken along the line V—V of FIG. 3. In FIGS. 3 and 5, numeral 16 designates a stop for preventing the closure member 15, which has been broken-off by snapping, from flowing into the blood components separator 4 together with the whole blood. The valve means of FIGS. 3 and 4 is in no way limiting and various types of valve means may be employed as long as the valve means can be easily opened by manual manipulation of its opening means from outside of the second tube 9. Other types of valve means employable in the present invention, include those disclosed in U.S. Pat. No. 4,294,247.

The membrane type blood components separator 4 has a plasma outlet and a blood cell outlet. A plasma collection reservoir 5 and a blood cell collection reservoir 6 for collecting blood cell enriched blood are connected to the plasma outlet of the separator 4 through a third tube 10 and to the blood cell outlet of the separator 4 through a fourth tube 11, respectively.

The type of a blood components separator 4 is not specifically restricted with respect to the material and shape of the membrane as long as the separator is capable of separating a plasma component efficiently. Any type of a membrane, such as a flat membrane and hollow membrane, may be used. Examples of materials of the membrane include cellulose acetate, polyvinyl alcohol, polymethyl methacrylate, polyethylene, polypropylene and polysulphone. It is requisite that the membrane be sterilized so that it can be used without washing with e.g. a physiologically isotonic solution and without priming operation by flowing, e.g. an isotonic sodium chloride solution for expelling dust and bubbles. As described later, it is preferred that the sterilization of the entire unit including the separator is performed by heating, for example, using an autoclave and therefore, it is preferred that a membrane be resistant to heat treatment. From this viewpoint, membranes made of polyvinyl alcohol, polyethylene, polypropylene and the like are preferred. With respect to the membrane which may be used in the present invention, reference may by made to, for example, U.S. Pat. No. 4,402,940, Japanese Patent Application Laid-Open Specification Nos. 52-152877 and 56-49157, and the like. The membrane incorporated in the blood components separator 4 may be either in a dry or wet state. In general, it is more preferred that the membrane be in a wet state irrespective of the type of a membrane material. The reason for this is as follows. In the case where the membrane is hydrophobic as in the case of those made of polyethylene and polypropylene, and the membrane is in a dry state, the membrane is apt to repel the blood, causing the filtration of whole blood through the membrane to be difficult. On the other hand, in the case where the membrane is hydrophilic as in the case of that made of polyvinyl alcohol and the membrane is in a dry state, there is a danger that hemolysis of the blood occurs.

In order to wet a membrane, the membrane may be moistened with a physiologically isotonic solution. The amount of the physiologically isotonic solution for moistening the membrane may preferably be A/100 g or less, preferably 0.3A/100 g to A/100 g, wherein A is a surface area of the membrane expressed in terms of cm$^2$. Examples of physiologically isotonic solutions include an anticoagulant as mentioned above, a physiological saline, a physiological salt solution such as Ringer's solution, and the like. In this connection, however, it should be noted that moistening of the membrane of the blood components separator is, on one hand, preferred from the viewpoints of prevention of hemolysis of the blood and enhancement of performance of the membrane as described above, but, on the other hand, it has a drawback in that the blood components separated by the membrane are disadvantageously caused to be diluted with a physiologically isotonic solution. In order to decrease such dilution, the amount of a physiologically isotonic solution to be used for moistening the membrane should be reduced. In this case, it is most preferred that an anticoagulant be employed as the physiologically isotonic solution for moistening the membrane in an amount such that the sum of the amount of the anticoagulant used for moistening the membrane and the amount of the anticoagulant contained in the blood collection bag is substantially equal to an amount of the anticoagulant to be used for preserving the blood of a quantity which is to be collected in the blood collection bag.

The minimum volume of a physiologically isotonic solution for moistening the membrane may be approximately equal to the volume of all the pores of the membrane, which volume can be theoretically calculated from the thickness, surface area and porosity of the membrane in the case of a hydrophobic membrane. On the other hand, in case the membrane is hydrophilic, since the membrane swells when an aqueous solution is applied to the membrane, the minimum amount of the physiologically isotonic solution required for moistening the membrane becomes a little larger than that required for moistening the above-mentioned hydrophobic membrane. In this connection, however, it should be noted that when an anticoagulant is used as the physiologically isotonic solution and the anticoagulant is employed in an increased amount enough for moistening the hydrophilic membrane, the amount of an anticoagulant which can be charged in the blood collection bag becomes small because the total amount of the anticoagulant contained in the blood collection bag and the amount of the anticoagulant used for moistening the hydrophilic membrane is determined depending on the amount of whole blood which is to be collected. The decrease in amount of the anticoagulant to be charged in the blood collection bag may lead to danger that the blood is coagulated during the collection of whole blood. On the other hand, it is not desirable to use a hydrophobic membrane because the hydrophilic membrane is poor in water retention and hence there is a danger that it dries up before use even if the membrane has been moistened. Thus, there is a dilemma even if either a hydrophilic membrane or a hydrophobic membrane is used. From the standpoint of elimination of such dilemma, it is most preferred to employ a composite porous membrane comprising a hydrophobic porous membranous matrix and a water-insoluble hydrophilic layer formed on the overall surface of the matrix. Examples of materials of the hydrophobic porous membraneous matrix include a polyolefin such as polyethylene and polypropylene. The formation of a water-insoluble hydrophilic layer on the overall surface of the matrix may be performed by, for example, coating of a water-insoluble hydrophilic polymer, introduction of a water-insoluble hydrophilic monomer by graft polymerization, coating of a water-insoluble hydrophilic monomer followed by polymerization, treatment with plasma, sulfonation, and the like. In this respect, reference may be made to, for example, European Patent Application Publication No. 0 203 459, British Patent Application Laid-Open Specification No. 2035133 and Japanese Patent Publication No. 61-39406 and PCT Patent Application Publication No. WO 84/00015. From the standpoint of the harmlessness to the human body, it is preferred that the water-insoluble hydrophilic layer be composed of a water-insoluble hydrophilic polymer comprised of hydrophilic monomeric units and hydrophobic monomeric units, and having a hydrophilic monomeric unit content of from 40 to 90% by weight based on the weight of the polymer. Preferred examples of the hydrophilic monomeric unit include those from monomer compounds having a hydrophilic functional group such as a hydroxyl group, a carboxyl group, an amide group, an amino group, a sulfonic group, an oxyethylene group or the like. Specific examples of such monomeric units include those from vinyl alcohol hydroxyethyl methacrylate, acrylic acid, acrylamide, vinylpyrrolidone, oxyethylene and the like. Preferred examples of the hydrophobic monomeric unit include those from monomer compounds having a hydrophobic functional group such as an alkyl group, an alkylene group, a halogen group, a phenyl group, a dimethylsiloxane group or the like. Specific examples of such monomeric units include those from ethylene, propylene, vinylidene fluoride, tetrafluoroethylene, vinyl chloride, vinylidene chloride, styrene dimethylsiloxane, ethylene terephthalate, bisphenol A carbonate, aminoundecanoic acid, aromatic urethanes and the like.

When a physiologically isotonic solution is introduced into the blood components separator 4 in order to moisten the membrane of the separator, it is preferred that the third tube 10 and fourth tube 11, which connect the plasma outlet and blood cell outlet of the blood components separator 4 to the plasma collection reservoir 5 and blood cell collection reservoir 6, respectively, be closed by means of a clamp or valve means of the type as described above before separation of the blood is carried out so that the physiologically isotonic solution is prevented from flowing downward to the plasma collection reservoir 5 and blood cell collection reservoir 6.

The blood cell collection reservoir 6 may contain a preservative for red cells. Examples of preservatives include ADSOL ® (a red cell preservation solution manufactured and sold by Travenol Laboratories, Inc., U.S.A.) and the like.

In the blood components collector unit of the present invention, only the cannula 1 has an open end for withdrawing whole blood from a donor, and the other constituting parts of the unit are all closed to external air. As shown in FIG. 1, the cannula 1, blood collection bag 2, and membrane type blood components separator 4 are linearly connected in this order through the first and second tubes 8 and 9, and the blood components separator 4 is then connected at its plasma outlet to the plasma collection reservoir 5 through the third tube 10 and connected at its blood cell outlet to the blood cell collection reservoir 6 through the fourth tube 11.

In the blood components collector unit of the present invention, each connection through each of the first to fourth tubes 8, 9, 10 and 11 at both ends thereof is in a fixed fashion, thereby providing unified connection. The connection may be attained by a customary method, for example, heat treatment, ultrasonication, adhesion by means of an adhesive and the like. The connection may also be attained by forming the entire unit of the present invention integrally by molding as described, for example, in U.S. Pat. No. 3,946,731 and Japanese Patent Application Laid-Open Specification No. 54-113998.

The materials of the blood collection bag 2, plasma collection reservoirs and blood cell collection reservoir 6 are not critical, but it is preferred that the bag 2 and reservoirs 5 and 6 be made of a flexible material. Generally, polyvinyl chloride is used as a material. The shapes of the blood collection bag 2, plasma collection reservoir 5 and blood cell collection reservoir 6 are also not critical. Generally, the shapes of them may be rectangular, oval or the like. The capacities of the blood collection bag 2, plasma collection reservoir 5 and blood cell collection reservoir 6 may generally be about 200 to 600 ml, about 100 to 400 ml and about 200 to 400 ml, respectively. The bag 2 and reservoirs 5 and 6 may preferably not be opaque but transparent or translucent.

The material of the first to fourth tubes is not critical and any material used for tubes of a conventional blood collection apparatus may be employed. Generally, polyvinyl chloride is used as a material of the tubes. The tubes may be flexible or rigid.

The length of each of the above-mentioned connecting tubes is determined so as to give a sufficient head for facilitating the fall of the collected blood in the blood collection bag 2 to the separator 4 and reservoirs 5 and 6 by the force of gravity at a blood flow rate at which the separating ability of the blood components separator is fully exhibited while not causing any damage to blood, such as hemolysis. The head may be varied according to the capacity of the blood collection bag 2, the inside diameters of the connecting tubes 8, 9, 10 and 11, the separating ability of the blood components separator 4 and the like. As mentioned above, the connecting tubes may be flexible or rigid. In order to give a sufficient head effectively, it is preferred to use a rigid material as a material of a tube. In the case where a rigid material is used, it is preferred that each tube comprise plural rigid tubes and they are connected alternately with flexible tubes so that the unit of the present invention can be folded up compactly in order to facilitate storage and transportation of the unit before use.

If desired, the blood components collector unit of the present invention may further comprise filtering means for removing leukocytes, which is provided between the valve means 3 and the membrane type blood components separator 4 or between the membrane type blood components separator 4 and the blood cell collection reservoir 6. The provision of such filtering means for removing leukocytes enables the whole blood to be separated into three kinds of components, i.e., plasma, leukocytes and a leukocyte-removed blood cell-enriched blood. Examples of the filtering means for removing leukocytes which may be used in the present invention include those disclosed in U.S. Pat. No. 4,330,410 and European Patent Application Publication No. 0 155 003. In the case where the blood components collector units of the present invention additionally includes a filtering means for removing leukocytes, a bag containing a physiological saline may be connected to the second tube 9 at its portion upstream the filtering means for removing leukocytes through a fifth tube. The fifth tube is closed by means of valve means of the type as described above before the separation of the blood is completed so that the physiological saline is prevented from flowing downward to the filtering means for removing leukocytes. After completion of the separation of blood utilizing the force of gravity, the valve means positioned in the fifth tube was opened and the physiological saline contained in the bag is flowed downward to the filtering means so that the blood remaining unfiltered in the filtering means is pushed downward, thereby to filter the remaining blood completely. The materials of the bag containing a physiological saline and the fifth tube are not critical. Generally, polyvinyl chloride may be used. The amount of the physiological saline to be contained in the bag is varied according to the type of the filtering means for removing leukocytes. Generally, the amount of the physiological saline may be about 40 to 50 ml.

The blood components collector unit of the present invention is packed in a container in a sterile state. The packing of the unit in a container in a sterile state may be conducted by any customary method. For example, the unit is packed in a container and sealed in the container, followed by sterilization by heat treatment, for example, by using an autoclave. Examples of materials for the container include a laminate film comprising a nylon sheet and, laminated thereon, aluminum foil and low density polyethylene sheet. Such laminate film is effective for preventing the anticoagulant in the blood collection bag 2 from escaping by evaporation.

The blood components collector unit of the present invention is of a substantially closed system in which only the cannula is open to the outside at its open end, and the unit is sterilized entirely. Therefore, the unit can be used immediately without any preparatory operation.

According to the present invention, it is not required for the donor to stay bound throughout the operation, but restrained only during the collection of whole blood into the blood collection bag 2 and, hence, burden on the donor can be decreased. By the use of the blood components collector unit of the present invention, the blood components can be collected from whole blood in a shortened period of time by an extremely simple operation substantially without any other auxiliary apparatus. The unit of the present invention is constructed as a substantially closed unit in which the only portion open to the outside is the cannula, which, however, is usually closed with a cap, and the unit is packed in a container in a sterile state. Therefore, the unit of the present invention is highly aseptic, and the possibility of germ contamination is very low as compared with the conventional blood components collection apparatuses which must be assembled from various separate parts just before use. Further, the unit of the present invention is completely closed during the blood components separation operation and therefore, the danger of germ contamination can be eliminated completely. Hence, according to the present invention, there can be obtained blood components having a long shelf life comparable to that of the blood components obtained by the conventional centrifugal separation method which is excellent in the shelf life of the separated components but has various disadvantages as mentioned before. In addition, by the use of the unit of the present invention, almost all the whole blood collected from the donor can be separated into useful blood components. Further, in the unit of the present invention, the separated blood cell is not intended to be returned to the donor and, hence, there is no need for additional safety measures such as bubble detectors and the like, and there is not any danger that the anticoagulant will be introduced into the donor.

Furthermore, since the blood components collector unit of the present invention is not only compact and light in weight, but also is always ready for immediate use without any other auxiliary apparatus, the unit can easily be conveyed and used anyplace, such as in an automobile and outdoors.

The present invention will now be described in more detail with reference to the following examples, which examples should not be construed to be limiting the scope of the present invention.

EXAMPLE 1

In a blood components collector unit as shown in FIG. 1, a blood collection bag 2 contained 46 ml of a CPD solution as an anticoagulant and 30 ml of sterile air, and had a capacity of 400 ml of whole blood.

Figure 2:
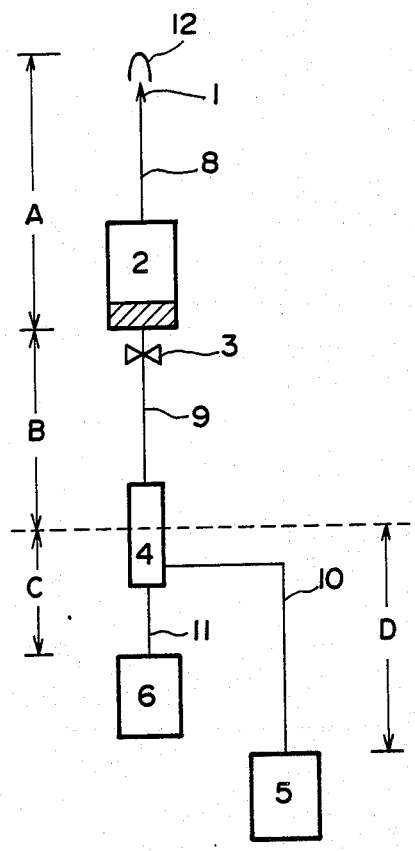
FIG. 2 is a schematic diagram of the unit of FIG. 1 which has been taken out of the container and is in use.

The unit of the present invention was taken out of a container 20. The unit was held so that a blood collection bag 2 positioned lower than a cannula 1, as shown in FIG. 2. The head (A) between the cannula 1 and the blood collection bag 2 was set so as not to give too high a blood flow rate at which the donor suffered, an overload. A cap 12 of a cannula 1 was taken off and the vein of a donor was punctured by means of the cannula. 400 ml of whole blood was collected from the donor into a blood collection bag 2 through the cannula 1 and a first tube 8. During the above-mentioned blood collection operation, a second tube 9 between the blood collection bag 2 and a membrane type blood components separator 4 was closed by means of valve means 3 which was positioned intermediate the length of and within the second tube 9 as illustrated in FIG. 3. As shown in FIG. 3, the valve means 3 had opening means 15 for opening the valve means. The opening means 15 was adapted to permit the opening of the valve means by manual manipulation from outside of the second tube 9. That is, by manipulating the opening means from outside of the second tube 9, the valve means was adapted to open, thereby enabling the collected blood in the blood collection bag to flow down into a blood components separator 4.

After 400 ml of whole blood was collected in the blood collection bag 2, the cannula 1 was taken off from the vein of the donor, and then the tip of the cannula was sealed with a cap 12. The collected whole blood was caused to be mixed with 46 ml of CPD solution as the anticoagulant contained in the blood collection bag 2. To mix the anticoagulant and blood cell, the blood collection bag 2 was subjected to manual operations such as mild shaking, and inverting.

Then, all the parts of the unit were held in the vertical direction as shown in FIG. 2. The head B between the blood collection bag 2 and blood components separator 4, head C between the blood components separator 4 and a blood cell collection reservoir 6 for collecting blood cell-enriched blood, and head D between the blood components separator 4 and a plasma collection reservoir 5 were set at 60 cm, 20 cm and 55 cm, respectively.

As the blood components separator 4, a plasma separator as disclosed in European Patent Application Publication No. 0 203 459 was used. Particularly, there was employed a plasma separator comprising 840 porous hollow fiber membranes each having an inner diameter of 340 $\mu$m, a membrane thickness of 50 $\mu$m, and an average pore diameter of 0.4 $\mu$m in terms of the value as obtained by a bubble point method in accordance with ASTM-F316-70. The total surface area of the membrane was 1800 $cm^2$. The porous hollow fiber membranes were composite porous membranes prepared by subjecting a high density polyethylene hollow fiber to stretching perforation to form a porous membranous hollow fiber matrix and coating an ethylene-vinyl alcohol copolymer on the overall surface of the porous membranous hollow fiber matrix. The composite porous membranes in the blood components separator 4 had been moistened with 10 ml of a CPD solution.

The valve means 3 was opened, thereby allowing the CPD-containing whole blood in the blood collection bag 2 to flow downward into the membrane type blood components separator 4 at an appropriate flow rate due to the head B. A plasma component of the whole blood was separated in the blood components separator 4, and then flowed into the plasma collection reservoir 5, while a blood cell-enriched blood separated from the whole blood, which had been unable to pass through the membrane pores, was flowed into the blood cell collection reservoir 6 for collecting a blood cell-enriched blood.

After completion of the separation utilizing the force of gravity, the blood remaining unseparated in the blood components separator and tubes was pushed downward by the pressure of sterile air in the blood collection bag, which pressure was produced by squeezing the blood collection bag, thereby separating the remaining blood completely.

Thus, the whole blood was separated into the desired components by an extremely simple operation while making no waste of blood. The whole operation time was about 30 min including the time for opening the container and for sticking a cannula in the vein.

As a result, about 170 ml of plasma and about 270 ml of blood cell-enriched blood were collected from the mixture of 400 ml of whole blood and 56 ml of an anticoagulant.

EXAMPLE 2

Separation of whole blood into blood components was conducted in substantially the same manner as in Example 1 except that a filtering means for removing leukocytes was provided between the blood collection bag 2 and the blood components separator 4.

As the filtering means for removing leukocytes, there was employed one as disclosed in Japanese Patent Application Laid-Open Specification No. 60-203267.

As a result of the separation operation, there were collected about 245 ml of leukocyte-removed blood cell-enriched blood and about 155 ml of plasma from a mixture of 400 ml of whole blood and 56 ml of CPD solution.

While an embodiment of the present invention has been described above with reference to the drawings and examples, various modifications and alterations can of course be made by one skilled in the art within the technical scope defined in the appended claims.

What is claimed is:

1. A blood components collector unit comprising:
a cannula,
a blood collection bag connected to said cannula through a first tube, said blood collecting bag containing an anticoagulant,
a membrane type blood components separator having a plasma outlet and a blood cell outlet, which separator is connected to said blood collection bag on its side remote from said cannula through a second tube,
said membrane type blood components separator having a membrane moistened with a physiologically isotonic solution which is employed in an amount of A/100 g or less wherein A is a surface area of said membrane expressed in terms of $cm^2$, valve means positioned intermediate the length of and within said second tube, which is in the closed state and has opening means for opening said valve means, said opening means being adapted to permit the opening of the valve means by manual manipulation from outside of said second tube, a plasma collection reservoir for collecting plasma, and a blood cell collection reservoir for collecting blood cell-enriched blood, said plasma collection reservoir and said blood cell collection reservoir being connected to said blood components separator at said plasma outlet through a third tube and at said blood cell outlet through a fourth tube, respectively, wherein each connection through each tube at both ends thereof is in a fixed fashion, thereby providing unified connection, and wherein said collector unit is packed in a container in a sterile state, thereby enabling the blood components collector unit to be stored aseptically for a prolonged period of time and to be readily used for collecting blood from a donor without rinsing the blood components collectors unit with a rinsing solution, leading to elimination of the danger of dilution of the blood components, and wherein said blood collection bag and said value means provide means for decreasing the burden on the donor by allowing the unit to be separated from a donor immediately after completion of the collection of blood from the donor to bag, while allowing continued separation of blood into blood components.

2. A blood components collector unit according to claim 1, wherein said physiologically isotonic solution comprises an anticoagulant.

3. A blood components collector unit according to claim 2, wherein the sum of the amount of said anticoagulant used for moistening said membrane and the amount of an anti-coagulant contained in said blood collection bag is substantially equal to an amount of the anticoagulant to be used for preserving the blood of a quantity which is to be collected in said blood collection bag.

4. A blood components collector unit according to claim 1, wherein said membrane of said membrane type blood components separator is a hydrophilic composite porous membrane comprising a polyolefin porous membranous matrix and a water-insoluble hydrophilic layer formed on the overall surface of said matrix.

5. A blood components collector unit according to claim 4, wherein said polyolefin is selected from the group consisting of polyethylene and polypropylene.

6. A blood components collector unit according to claim 5, wherein said water-insoluble hydrophilic layer is composed of a water-insoluble hydrophilic polymer comprised of hydrophilic monomeric units and hydrophobic monomeric units, and having a hydrophilic monomeric unit content of from 40 to 90% by weight based on the weight of the polymer.

7. A blood components collector unit according to claim 4, wherein said polyolefin is polyethylene, and said water-insoluble hydrophilic polymer is an ethylene-vinyl alcohol copolymer.

8. A blood components collector unit according to claim 1, wherein said blood collection bag contains a sterile gas.

9. A blood components collector unit according to claim 8, wherein said sterile gas is selected from the group consisting of a sterile air and a sterile nitrogen gas.

10. A blood components collector unit according to claim 1, which further comprises a filtering means for removing leukocytes, said filtering means being provided between said valve means and said blood components separator and/or between said blood components separator and said blood cell collection reservoir.

* * * * *